US00PP10618P

United States Patent [19]

Austin

[11] Patent Number: Plant 10,618

[45] Date of Patent: Sep. 29, 1998

[54] SHRUB ROSE PLANT NAMED 'AUSCOOK'

[75] Inventor: David Charles Henshaw Austin, Albrighton, England

[73] Assignee: David Austin Roses Limited, Albrighton, England

[21] Appl. No.: 788,745

[22] Filed: Jan. 24, 1997

[51] Int. Cl.[6] ..... A01H 5/00

[52] U.S. Cl. ..... Plt./1

[58] Field of Search ..... Plt./1, 22, 11, Plt./19, 27

*Primary Examiner*—Howard J. Locker

*Attorney, Agent, or Firm*—Klarquist Sparkman Campbell Leigh & Whinston, LLP

[57] ABSTRACT

A shrub rose plant having the unique combination of its dark pink flowers, attractive rounded flower which opens to show stamens, strong fragrance, repeat flowers, and attractive shrubby, arching growth.

1 Drawing Sheet

The present invention relates to a new and distinct variety of shrub rose plant of the *Rosa hybrida* class which was originated by me by crossing two unnamed seedlings.

The primary objective of this breeding was to produce a new shrub rose variety having greater repeat flowering, a more fully double flower, and increased strength and height. The objective was substantially achieved, along with other desirable improvements, as evidenced by the following unique combination of characteristics that are outstanding in the new variety and that distinguish it from its parents, as well as from all other varieties of which I am aware:

1. Strong dark pink flowers;
2. Attractive rounded flower which opens to show stamens;
3. Strong fragrance;
4. Repeat flowers well;
5. Attractive shrubby, arching growth.

Asexual reproduction of this new variety by budding, as performed at Albrighton, Wolverhampton, England, shows that the foregoing and all other characteristics and distinctions come true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed description of my new rose cultivar with color descriptions using terminology in accordance with The Royal Horticultural Society (London) Colour Chart, except where ordinary dictionary significance of color is indicated.

Parentage:

*Seed parent.*—Unnamed seedling.

*Pollen parent.*—An unnamed seedling of Leander× Chaucer.

Classification:

*Botanical.*—*Rosa hybrida*.

*Commercial.*—Shrub.

Flower

Observations made from specimens grown in a garden environment at Albrighton, Wolverhampton, England in July 1996.

Blooming habit: Recurrent.

Bud:

*Size.*—About 30 mm long when the petals start to unfurl.

*Form.*—The bud form is short, blunt topped.

*Color.*—When sepals first divide, bud color is Red-Purple Group 65B. When half blown, the upper sides of the petals are Red-Purple Group 68B; and the lower sides of the petals are Red-Purple Group 68A.

*Sepals.*—Color: Green Group 143C. Surface texture: Hairy and waxy. There are three normally appendaged sepals. There are two unappendaged sepals with hairy edges.

*Receptacle.*—Color: Yellow-Green Group 144B. Shape: Funnel. Size: Medium, about 10 mm×6 mm. Surface: Smooth.

*Peduncle.*—Length: Short, about 25–35 mm. Surface: Smooth, slighty prickly. Color: Medium green (Yellow-Green Group 146B). Strength: Slightly bending.

Bloom:

*Size.*—Medium. Average open size is 50–60 mm.

*Borne.*—Several together in clusters of three to twelve.

*Stems.*—Long, normal strength. Average length is about 550–650 mm.

*Form.*—When first open: Cupped. Permanence: Outer petals curl back.

*Petalage.*—Number of petals under normal conditions: Average 59.

*Color.*—The upper sides of the petals are Red-Purple Group 68B and Red-Purple Group 73B. The reverse sides of the petals are Red-Purple Group 62C. The base of each petal is Yellow Group 4A. The major color on the upper sides is Red-Purple Group 68B.

*Variegations.*—None.

*Discoloration.*—The general tonality at the end of the first day: No change. At the end of the third day: No change.

*Fragrance.*—Good, Old Rose fragrance.

Petals:

*Texture.*—Medium.

*Shape.*—Outer round, inner oval.

*Form.*—Tips slightly recurved.

*Arrangement.*—Irregular, imbricated. Open cupped, with a very few, small petaloids in the center.

*Persistence.*—Petals drop off cleanly before drying.

*Lastingness.*—On the plant: Long, about 5–7 days. As a cut flower: Fair, about 3 days.

Reproductive parts:

*Anthers.*—Size: Medium. Quantity: Many. Color: Yellow. Arrangement: Regular around styles.

*Filament.*—Color: Yellow pink.
*Pollen.*—Color: Gold yellow.
*Styles.*—Color: Red Group 52A.
*Stigmas.*—Color: Whitish yellow.

Form: Shrub.

Growth: Medium, with upright branching. Mature plant about 90 cm in height and 70 cm in width.

Foliage:
*Number of leaflets on normal mid-stem leaves.*—5.
*Size.*—About 60 mm long×40 mm wide.
*Quantity.*—Normal.
*Color.*—New foliage: Upper surface: Yellow-Green Group 147A. Lower surface: Grey-Purple 184A. The new foliage is suffused with Greyed-Purple Group 183B. Old foliage: Upper surface: Green Group 137A. Lower surface: Yellow-Green Group 147B.

Leaflets:
*Shape.*—Broadly oval.
*Texture.*—Upper side: Glossy.
*Edge.*—Serrated.
*Serration.*—Single, small.
*Petiole rachis.*—Color: Reddish.
*Petiole Underside.*—Rough.
*Stipules.*—Medium, serrated (about 20 mm long from tip to where it joins stem).
*Disease resistance.*—Resistant to mildew and black-spot under normal growing conditions at Albrighton, Wolverhampton, England.

Wood:
*New wood.*—Color: Light green; dark green nearer the bottom of new growth. Bark: Smooth.
*Old wood,*—Color: Green. Bark: Smooth.

Prickles:
*Quantity.*—On main canes from base: Ordinary. More abundant toward the base of the main stem. On laterals from main canes: Few.
*Form.*—Medium, short, straight.
*Color when young.*—Greyed-Purple Group 187B at the base and Yellow-Green Group 146C at the point.

Small Prickles:
*Quantity.*—On main stalks: Few. On laterals: Few.
*Color.*—Grey-Brown Group 199C.

I claim:

1. A new and distinct variety of shrub rose plant of the *Rosa hybrida* class, substantially as herein shown and described, characterized particularly as to novelty by the unique combination of its dark pink flowers; attractive rounded flower which opens to show stamens; strong fragrance; repeat flowering; and attractive shrubby, arching growth.

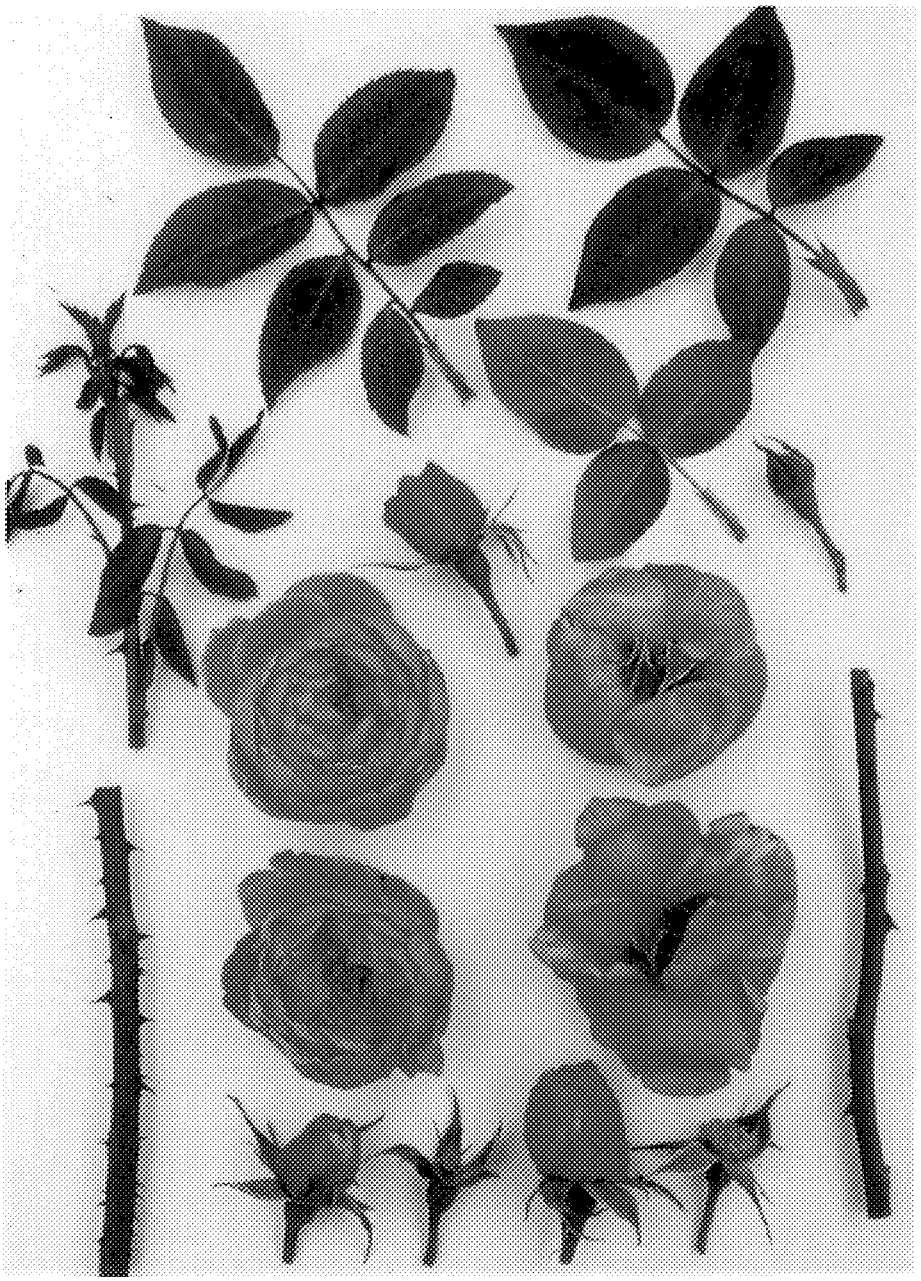

* * * * *